(12) United States Patent
Lundgren

(10) Patent No.: US 8,128,402 B2
(45) Date of Patent: Mar. 6, 2012

(54) TUBULAR BONE ANCHORING ELEMENT

(75) Inventor: Dan Lundgren, Hovås (SE)

(73) Assignee: Nobel Biocare Services, AG, Zurich-Flughafen (CH)

( * ) Notice: Subject to any disclaimer, the term of this patent is extended or adjusted under 35 U.S.C. 154(b) by 0 days.

(21) Appl. No.: 10/591,372

(22) PCT Filed: Mar. 3, 2005

(86) PCT No.: PCT/SE2005/000308
§ 371 (c)(1),
(2), (4) Date: Jun. 25, 2007

(87) PCT Pub. No.: WO2005/084578
PCT Pub. Date: Sep. 15, 2005

(65) Prior Publication Data
US 2008/0003539 A1     Jan. 3, 2008

(30) Foreign Application Priority Data
Mar. 5, 2004 (SE) ...................... 0400546

(51) Int. Cl.
*A61C 8/00* (2006.01)
(52) U.S. Cl. ........................................ 433/174
(58) Field of Classification Search ............. 433/173, 433/174
See application file for complete search history.

(56) References Cited

U.S. PATENT DOCUMENTS

| | | | |
|---|---|---|---|
| 3,499,222 A * | 3/1970 | Edelman et al. | 433/174 |
| 3,732,621 A * | 5/1973 | Bostrom | 433/174 |
| 3,866,510 A | 2/1975 | Eibes et al. | |
| 4,180,910 A | 1/1980 | Straumann et al. | |
| 4,359,318 A | 11/1982 | Gittleman | |
| 4,447,209 A | 5/1984 | Sutter | |
| 4,531,916 A | 7/1985 | Scantlebury et al. | |
| 4,657,510 A | 4/1987 | Gittleman | |
| 4,790,753 A | 12/1988 | Fradera | |
| 4,960,381 A | 10/1990 | Niznick | |
| 4,960,391 A | 10/1990 | Beinhaur | |
| 5,061,181 A | 10/1991 | Niznick | |
| 5,071,351 A | 12/1991 | Green | |
| 5,076,788 A | 12/1991 | Niznick | |
| 5,259,398 A * | 11/1993 | Vrespa | 128/898 |
| 5,312,256 A | 5/1994 | Scortecci | |
| 5,366,374 A | 11/1994 | Vlassis | |

(Continued)

FOREIGN PATENT DOCUMENTS
EP 1 145 691 4/2000
(Continued)

OTHER PUBLICATIONS

International Search Report for PCT Application No. PCT/US2005/002717 filed Jan. 28, 2005.

(Continued)

*Primary Examiner* — Ralph Lewis
(74) *Attorney, Agent, or Firm* — Knobbe, Martens, Olson & Bear, LLP.

(57) ABSTRACT

A bone anchoring element comprises a tubular implant to be inserted into bone tissue for anchoring a prosthetic component located outside the bone. The implant has a compact, impermeable side wall (2) and is open at one end while the other end is closed by a compact impermeable end wall portion with attachment for prosthetic component on the outside thereof.

66 Claims, 14 Drawing Sheets

U.S. PATENT DOCUMENTS

| | | | |
|---|---|---|---|
| 5,433,607 A | | 7/1995 | Schmid et al. |
| 5,470,230 A | | 11/1995 | Daftary et al. |
| 5,503,187 A | * | 4/1996 | Simmons et al. ............... 138/89 |
| 5,571,017 A | | 11/1996 | Nlznick |
| 5,591,029 A | * | 1/1997 | Zuest ........................... 433/173 |
| 5,622,500 A | | 4/1997 | Niznick |
| 5,667,384 A | | 9/1997 | Sutter |
| 5,702,346 A | | 12/1997 | Lazzara et al. |
| 5,762,500 A | | 6/1998 | Lazarof |
| 5,816,813 A | * | 10/1998 | Hansson et al. ............... 433/174 |
| 5,871,356 A | * | 2/1999 | Guedj ........................... 433/174 |
| 5,989,028 A | | 11/1999 | Niznick |
| 6,213,775 B1 | | 4/2001 | Reipur |
| 6,287,117 B1 | | 9/2001 | Niznick |
| 6,394,809 B2 | | 5/2002 | Rogers et al. |
| 6,953,426 B2 | | 10/2005 | Barber et al. |
| 2001/0004711 A1 | | 6/2001 | Lazzara et al. |
| 2002/0160335 A1 | | 10/2002 | Ashman et al. |
| 2005/0042574 A1 | | 2/2005 | Lazarof |
| 2005/0164146 A1 | | 7/2005 | Cantor |
| 2006/0115791 A1 | | 6/2006 | Carvalho |
| 2007/0292820 A1 | | 12/2007 | Canter |
| 2008/0003539 A1 | | 1/2008 | Lundgren |
| 2008/0044794 A1 | | 2/2008 | Brajnovic |
| 2009/0081612 A1 | | 3/2009 | Jorneus et al. |

FOREIGN PATENT DOCUMENTS

| | | |
|---|---|---|
| EP | 1952781 A3 | 9/2008 |
| FR | 2 737 847 A | 2/1997 |
| FR | 2 783 700 | 3/2000 |
| GB | 1 203 093 | 8/1970 |
| JP | 56-136545 | 10/1981 |
| JP | 5-505952 | 3/1991 |
| WO | WO 91/14404 A | 10/1991 |
| WO | WO 01/26579 | 4/2001 |
| WO | WO 2005/072640 A1 | 8/2005 |
| WO | WO 2005/084578 A1 | 9/2005 |

OTHER PUBLICATIONS

International Preliminary Report on Patentability for Application No. PCT/US2005/002717 filed Jan. 28, 2005.
European Examination Report dated Dec. 8, 2006 for Application No. EP05706134 filed Jan. 28, 2005.
International Search Report for PCT Application No. PCT/SE2005/000308 filed Mar. 3, 2005.
International Preliminary Report on Patentability for PCT Application No. PCT/SE2005/000308 filed Mar. 3, 2005.
European Examination Report dated Sep. 3, 2007 for Application No. EP05722178 filed Mar. 3, 2005.
European Search Report for European Application No. EP08005017 filed Jan. 28, 2005.
European Search Opinion for European Application No. EP08005017 filed Jan. 28, 2005.
Office Action for U.S. Appl. No. 11/035,266, dated Jun. 15, 2009.
Jul. 28, 2010 Notice of Allowance for U.S. Appl. No. 11/035,266.
Dec. 12, 2009 Non-final office action for U.S. Appl. No. 11/035,266.
Jul. 26, 2010 Final office action for U.S. Appl. No. 10/587,497.
Mar. 3, 2010 Non-final office action for U.S. Appl. No. 10/587,497.

* cited by examiner

● = stop marking for D and E

A = compact cylinder ▨ 100 %

B = compact ▨ > 50 % ; tube < 50 %

C = compact ▨ ≈ 20 % ; tube ≈ 80 %

D = tube ☐ = 100 % according to the invention

E = tube ☐ > 120 % according to the invention

BIK (bone-implant contact) = E>D>C>B>A

TUBULAR BONE ANCHORING ELEMENT

BACKGROUND

1. Field of the Inventions

The invention relates to a tubular bone anchoring element (implant) for prosthetic constructions.

2. Description of the Related Art

It is previously known to anchor temporarily or permanently for example epitheses and hearing aids as well as tooth crown and tooth bridge constructions by means of oseo-integrated implants, often via extension units, so called abutments, perforating mucous membrane. The implants most often comprise compact threaded screws, which are screwed into the bone after a screw hole has been drilled. Either the implants are allowed to be oseo-integrated after covering by mucous membrane and are then connected with abutments after perforation of the mucous membrane, or the implants are connected directly to the abutments thereof or the prosthetic construction.

DT 2628485 A1 describes an arrangement for anchoring artificial teeth as a tubular structure. Both the side wall and the end wall of the tube are perforated so that the lumen of the tube is in direct connection with the bone tissue outside the tube (see FIG. 19), or the wall is porous to be able to let through liquid and tissue components from the bone as well as covering connective tissue. This involves a very great risk for contamination between the mouth cavity and the lumen of the tube if an infection arises around the implant. If there additionally arises some bone resorption around the implant, as is most often the case the consequences can be devastating for the implant when the infection and bone resorption extend to the lumen of the implant via hollows and porosities in the implant wall. This prior art implant has no threads neither on the inside surface nor on the outside surface of the sidewall but it is stated that there may be a helical ridge on the outside surface. The implant is substantially intended to be hacked or pressed down into a trephine-drilled groove. The lumen thereof moreover has a bone contact surface. The implant referred to cannot provide conditions of bone enlargement. Moreover it has preferably an outside diameter of only 4 mm.

A less immediate example of an implant is disclosed in WO 96 19 947. This implant certainly is tubular but only at the apical third part thereof, i.e. the third part most remote from the tooth crown. The upper part located adjacent the tooth crown is compact and is received by a blind hole for a screw attachment for the abutment of the tooth crown. This means that this implant has a small bone contact surface and requires removal of a considerable amount of bone at the insertion of the implant. The small extension of the apical cavity implies that the implant does not provide conditions for bone enlargement. It is not provided with threads neither on the outside surface nor on the inside surface of the sidewall. Also this implant preferably has an outside diameter of only 4 mm.

EP 0 083 558 describes a bone anchoring element comprising a tubular implant to be inserted into bone tissue for anchoring a prosthetic component located outside the bone said implant being open at one end which is intended to be inserted into the bone tissue while the implant at the other end, intended to be directed towards portions located outside the bone tissue is closed by a compact impermeable end wall portion having an attachment for the prosthetic component on the outside thereof the lumen extending from the open end through the total implant to the end wall portion so that the lumen after insertion of the implant in the bone tissue includes at least the total portion of the implant, which is intended to be anchored in the bone tissue.

SUMMARY OF THE INVENTION

The bone-anchoring element according to the invention is of this kind and the object thereof is to provide a bone-anchoring element having exceptional support contact between bone and implant so that there is obtained a great primary stability and a great torsional resistance also at installation in bone tissue having a limited bone height. A secondary object then is to effect the insertion of the implant at a minimum of bone cutting.

The bone anchoring element according to the invention as defined in claim 1 is characterized in that the implant has a compact impermeable side wall with an inside or outside stop to be engaged with the bone tissue in order to define an end position for the implant when being inserted into the bone tissue, and that the lumen of the implant includes also a cavity located in the end wall portion and open towards the lumen, the lumen as a consequence thereof having such extension that it after insertion of the implant into the bone will be located also above the bone level established around the implant.

Due to the shape thereof the implant provides an exceptionally great contact between bone and implant in relation to the length (height) and diameter thereof an exceedingly small removal of bone in connection with the installation of the implant being required. This makes the implant particularly suited for installation in bone tissue having a limited bone height and particularly in situations where the extension of the bone sidewise in relation to the direction of insertion of the implant is relatively large. Due to its shape and potentially large contact surface against adjacent bone the implant will have a unique primary stability and therefore can effectively take up vertical forces as well as side forces immediately after installation of the implant in the bone.

Further features of the invention are defined in the dependent claims.

The inside side wall surface of the implant in the closed end of the tube can form a conical ceiling or a cupola so that the lumen of the tube completely or partly fills the tower which forms the closed portion of the implant. This lumen after the installation of the implant in the bone will be located above the bone level established around the implant. Shortly after insertion of the implant and oseo integration thereof the lumen will be filled by ingrowing bone from the bone surface in the implant tube. That bone ingrowth takes place from bone surfaces bordering on apertures in titanium cupolas or titanium tubes has been shown in a plurality of studies on animals (Lundgren D. et al, 1995, Lundgren AK. 1999) as well as human beings (Hämmerli et al, 1996). By the bone ingrowth the contact surface of the implant against the bone will be further increased in relation to prior art cylindrical tubular or compact implants. The implant presented herein thus can be said to have the unique property to be bone enlarging, i.e. it provides conditions for regeneration of corporal bone in connection with existing bone but outside the original bone contour. This improves also successively anchoring of the implant by enlarged contact surface towards the bone without it being necessary to make use of the deeper portions of the bone.

Summarizing the unique design of the implant thus provides several advantages. These include extremely large bone contact surface and low invasivity, i.e. only relatively superficial bone portions have to be engaged. Moreover, the implant will be anchored substantially in the outer bone layer which has a large proportion of compact bone, i.e. bone with high bone density which increases the primary stability and the torsional resistance, which also is promoted by the extension of the implant sidewise which is also favourable considering the load receiving ability of the implant. The bone building properties of the implant are added to this.

The implant does not require an abutment between the implant and the construction to be anchored by the implant. Preferably the implant has threads on the outside as well as the inside of the sidewall and are then screwed into the bone. These threads can be synchronized and preferably have double entrances in order to allow screw attachment as rapidly as possible. Alternatively, the total inside side wall surface or parts thereof can be provided with micro threads and also the upper portion of the outside sidewall surface. Studies have shown that micro threads are particularly suitable in order to avoid loss of bone tissue about that portion of the implant, which penetrates the bone in the border zone at the overlying soft tissue.

The implant provides a bone contact surface, which is at least two times that of a compact cylindrical implant with a corresponding length and diameter. Also in situations with small bone height the implant despite its in that case small length (height) provides a bone contact surface which is substantially larger than that of a conventional cylindrical full-length implant (10 mm) with normal diameter (4 mm) and therefore can easily take up sufficient load in order to support the prosthetic construction.

The implant requires a bone cutting which is only about a fifth to a third of that for a compact cylindrical implant of a corresponding length and diameter and about a fourth to half of that for a compact implant of conventional length and diameter (10×4 mm).

A combination of small bone cutting and large bone contact surface provides a bone implant quotient, which is substantially greater than that of compact implants. Likely, this provides a greater propioceptive sensitivity and thus an earlier reaction on applied occlusive forces which should be a protection against mechanical overload.

Location of the implant so that the walls thereof are a tangent to the transition zone between compact and spongy bone moreover causes that the implant during the early integration is not sensitive to too low, spongy bone density (large marrow spaces).

An implant having a large diameter moreover provides a mechanical primary stability, which is of importance at immediate loading waiting for the biological bone reaction which takes place after installation of the implant and in the long run secures the oseo integration of the implant.

The large bone contact surface causes that the implant can be inserted into bone with a very low bone height, for example the scull bone and the bone of the lower jaw above the mandibular canal with the vessel nerve string thereof, and the bone of the upper jaw below the jaw cavities.

The tubular shape of the implant by the large bone contact surface provides a superior anchoring and resistance against vertical as well as horizontal forces and the often large diameter thereof provides a special ability to withstand these forces. This means that the implant with good prognosis can be inserted with a substantial inclination in relation to the main force direction.

The tubular shape of the implant with a closed ceiling which after installation of the implant will be located above the bone level established around the implant, means that the implant can form its own bone by the bone inside the implant growing up and filling the space under the ceiling of the implant, which further increases the bone contact of the implant. Alternatively, this space already at the installation of the implant can be filled with corporal bone in form of bone particles, which are collected in connection with trephine drilling of the implant seat. Another alternative is to fill the space with a bone substitute possibly mixed with corporal bone. These measures are intended to accelerate the establishment of the largest possible bone contact. A further alternative is to supply bone stimulating means such as BMP (bone morphogenetic protein) or other similar bone stimulating means. Further other measures include topographic and/or chemical modifications of the surface of the implant in general and particularly the inside surface thereof. It is previously known to stimulate to increased and more rapid bone formation by means of such methods. The unique feature of the implant presented herein is however the protected inner environment which minimizes disturbances in form of infections and mechanical influence on the organization of blood coagulation and other healing processes. A plurality of studies have shown that spaces defined by titanium walls and with simultaneous contact with living bone provides the possibility of a consequent bone formation in the entire closed space. Particularly pronounced is this bone formation along the walls of the space and this is true also when the space is located in spongy bone (Lundgren D. et al 1995, Lnddgren AK. 1999)

The outside diameter of the implant can vary from 4 to 16 mm, preferably from 6 to 10 mm. The length can vary from 2 to 16 mm, preferably from 3 to 8 mm. The implant consists of a material with sufficient biocompatibility and strength in order to be able to permanently anchor dental components 10 (as illustrated in FIG. 1D) such as tooth crowns, tooth bridges, tooth prostheses 11, (as illustrated in FIG. 1A), or epitheses of different kinds such as hearing aids, substitutes for body portions, transmitters or receivers for electric functions or radio functions. Examples of suitable materials are ceramics, metals or plastics or combinations thereof. An actual suitable metal is titanium of suitable quality. The invention also relates to a method for insertion of the implant into bone tissue wherein a recess is established in the bone tissue and the tubular portion of the implant is inserted into the recess and is anchored therein. The implant is inserted into the bone tissue through an opening in soft tissue which covers the bone tissue to a depth in the bone tissue at which the end wall portion of the implant is located at or above the surface of the bone tissue outside the recess.

The tubular implant according to the invention and the method for the insertion thereof in a jaw bone (or another suitable bone) now will be described in more detail reference being made to the accompanying drawings, in which

DETAILED DESCRIPTION OF THE PREFERRED EMBODIMENTS

Figure 1:
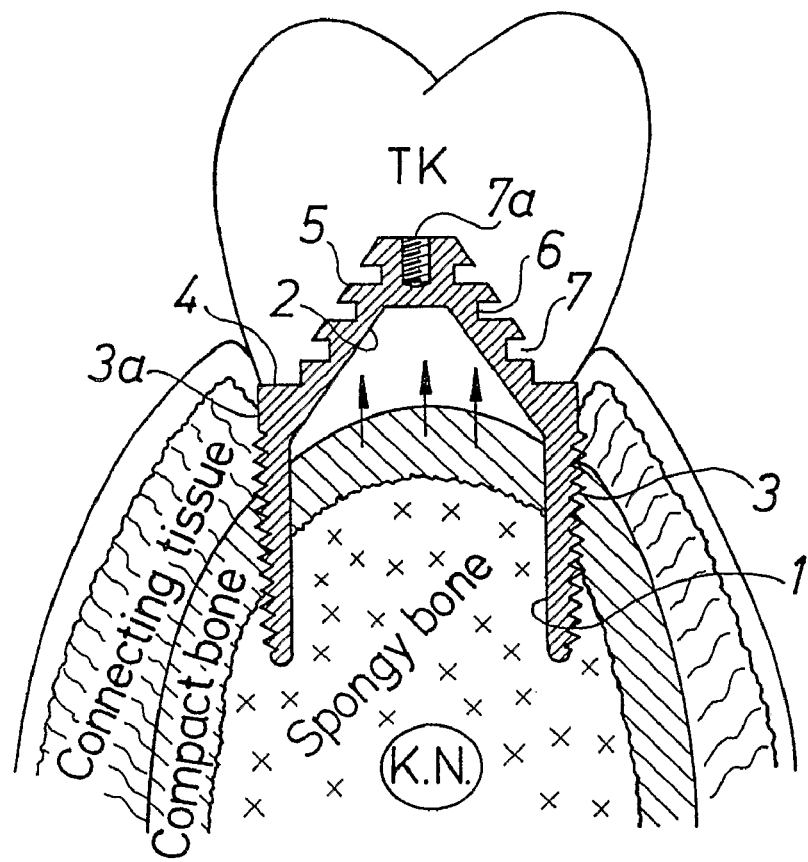
FIG. 1 is a vertical cross-sectional view of an embodiment of the implant according to the invention, which is inserted into bone tissue covered by soft tissue (connective tissue and epithelium)

In FIG. 1 an embodiment of the implant according to the invention is inserted into bone tissue, which is covered by soft tissue (connective tissue and epithelium). It has the shape of a tubular cylinder open downwards with an inner sidewall surface 1, which at the top joins an inner closed ceiling 2 which is shaped as an upwards tapering or truncated cone or a cupola. The inner side wall as well as the cone or cupola shaped ceiling preferably has small horizontal threads 1a, as illustrated in FIG. 1 A, and/or vertical threads, or horizontal grooves 1b, as illustrated in FIG. 1B, and/or vertical grooves 1c, as illustrated in FIG.1C, and/or are treated by different means and methods in order to present by modified topography a desired surface roughness, or by chemical influence to present a surface which is particularly attractive for surrounding bone tissue. The outer side wall surface 3 forms threads. In the embodiment shown the outer surface of the cylinder side wall converges slightly towards the lower open end of the cylinder. This side wall surface can, however, also be straight, i.e. non-convergent except in the lowermost portion thereof.

Figure 1A:
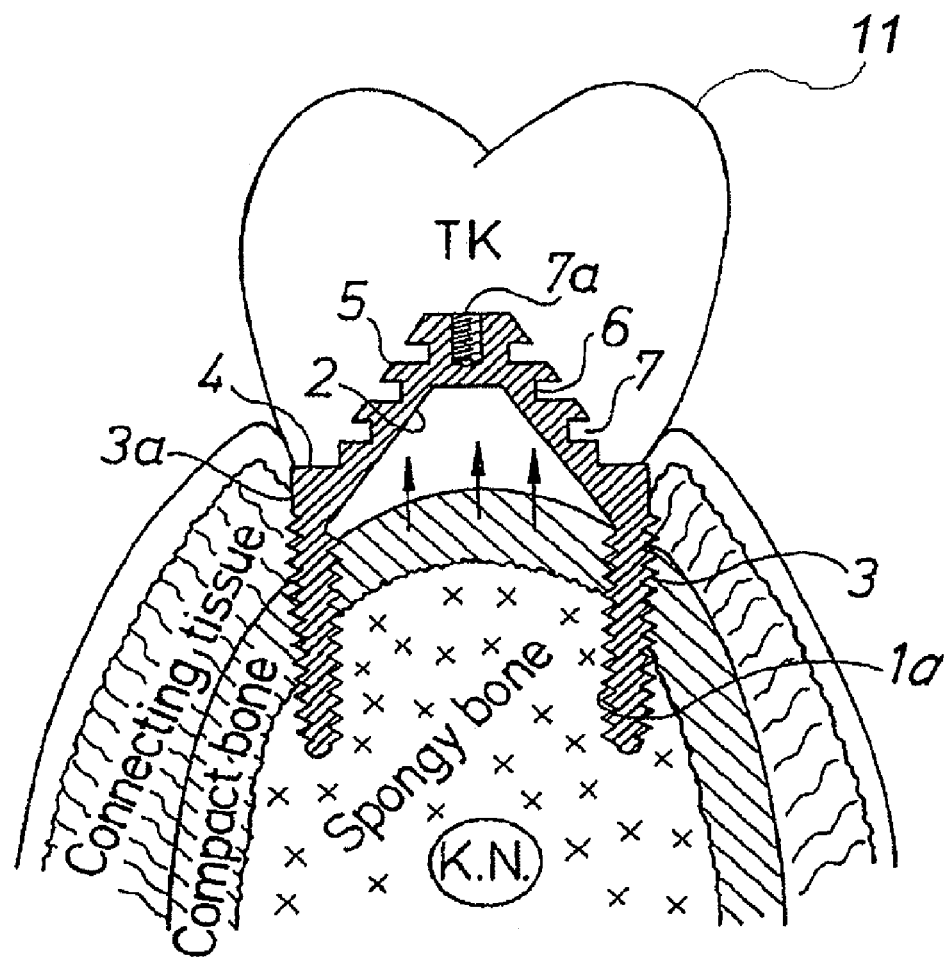
FIG. 1A is a schematic vertical cross-sectional view of an embodiment of an implant, illustrating threads, grooves, or vertically extending grooves on the inner surface.
Figure 1B:
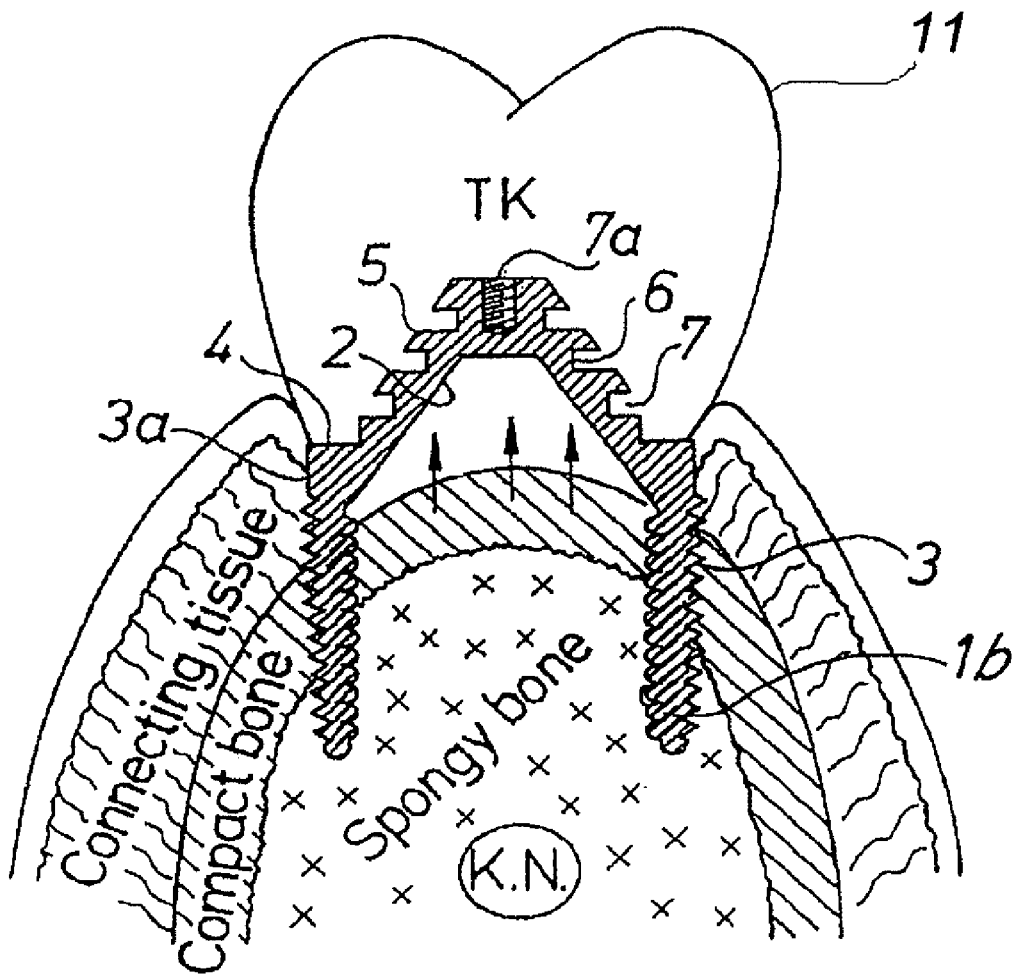
FIG. 1B is a schematic vertical cross-sectional view of an embodiment of an implant, illustrating grooves on the inner surface.
Figure 1C:
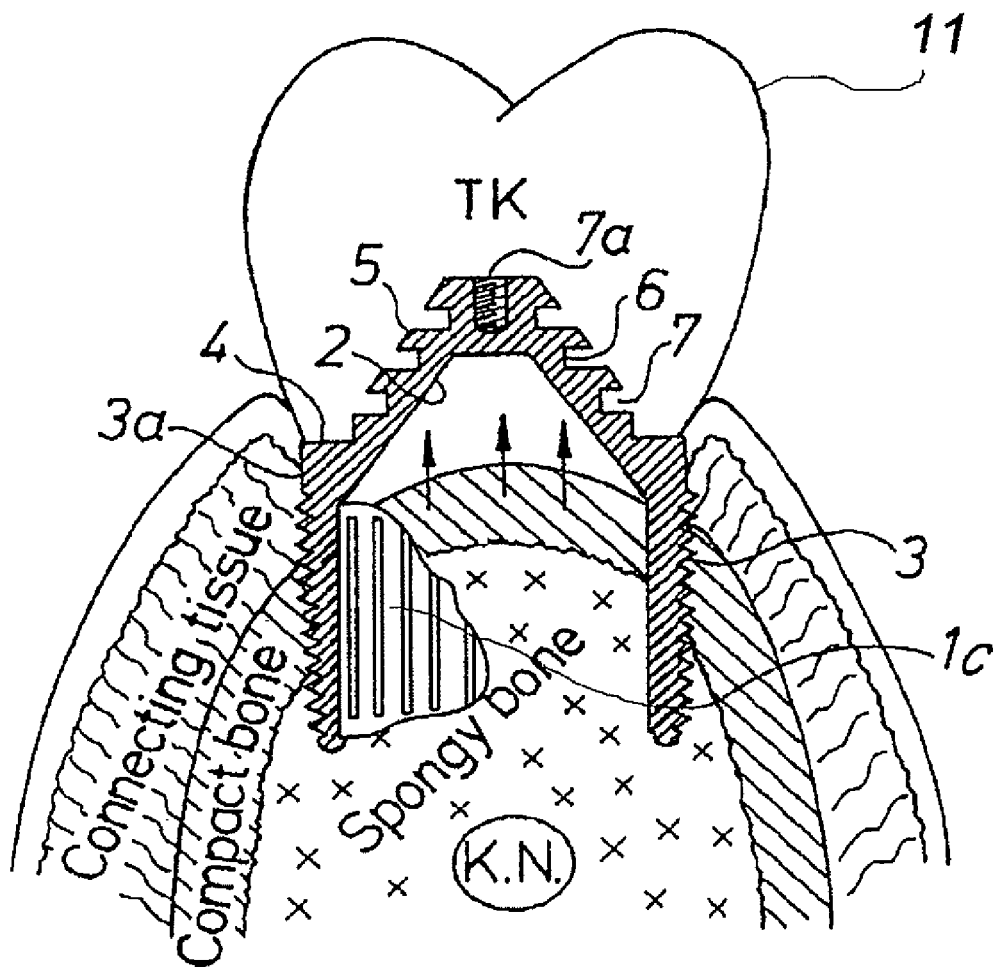
FIG. 1C is a schematic vertical cross-sectional view of an embodiment of an implant, illustrating vertically extending grooves on the inner surface.
Figure 1D:
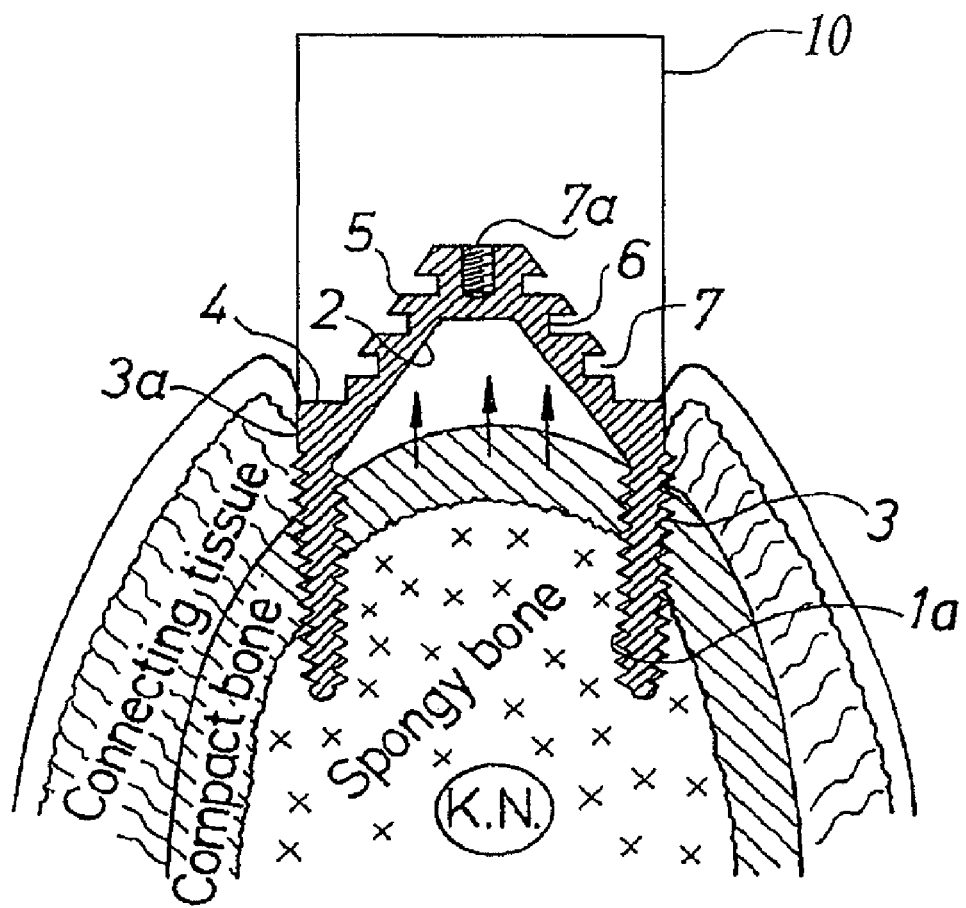
FIG. 1D is a schematic vertical cross-sectional view of an embodiment of an implant, illustrating a dental component coupled to the implant.

In another embodiment both the outer and the inner surface of the side wall are provided with synchronous threads, as illustrated in FIG. 1A, preferably with double entrances for rapid screwing. The two side wall surfaces can also be provided with synchronic micro threads or the inner surface can form micro threads and the outer can form a combination of conventional threads and micro threads these being located on the upper portion of this surface.

The threaded outer surface of the sidewall at the top joins a surface 3a which is smooth or provided with very small horizontal grooves or ridges or has another structure which binds optimally to surrounding soft tissue. In the embodiment shown the outer surface of the side wall is straight but it can also be converging or diverging upwards. Said surface at the top joins a smooth horizontal shoulder 4 on which the actual tooth crown TK rests. The shoulder towards the centre joins an upwards converging surface 5 which forms a tower that at the bottom thereof has six vertical side surfaces 6. The outer surface of the tower is provided with horizontal grooves 7 for cement retention of the tooth crown and terminates at the top in a horizontal plane in which there can be provided a threaded blind hole 7a. The vertical surfaces arranged on the sides of the tower resist rotation of the cemented (and possibly also screw fastened) tooth crown but are also motivated in order that it would be possible to establish a key engagement for screwing the implant into the bone in a rational manner.

Surfaces 1 and 3 of the side wall preferably are given a micro topography which promotes bone formation and bone compacting in connection with the surface as rapidly as possible. This can be achieved by means of grooves and ridges of optimum size or by means of etching, milling, electrolyses treatment or in another way in order to provide the correct "roughness" for maximum bone binding. The surface can also be treated chemically by entrainment of fluorine, calcium ions or in another way in order to further improve the binding to adjacent bone tissue.

The tube implant according to the invention avoids to interfere with the mandibular canal KN owing to the small length (height) thereof in spite of small bone height.

The implant shall be provided with a stop mark to define an end position for the implant at insertion into the bone tissue. This stop mark can comprise an inside or outside stop shoulder, which can be formed by the inside of the end wall and can be engaged with the bone tissue.

The intraoral jaw bone crest often has a generous width when the bone height is small, which favours tubular implants having a large diameter. Such an implant then can be located so that the side wall thereof buccally (towards the cheek) and lingually (towards the tongue) preferably involve the transient zone between the outer cortical (compact) bone and the intermediate spongy (marrow rich) bone. This zone has plenty of bone forming cells and at the same time allows optimum use of the dense, compact bone, which in studies has been found to promote stability and torsional resistance of the implant due to the fact that this bone has a more or less continuous contact with the implant (Meredith N. 1997).

Figure 2:
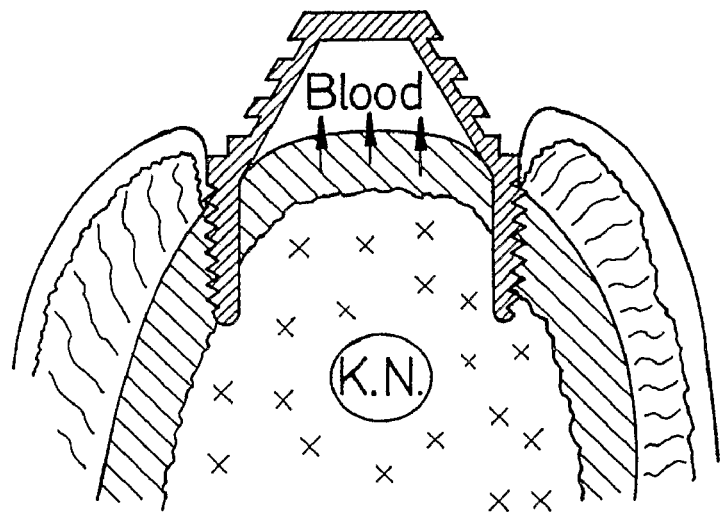
FIG. 2 is a similar view as FIG. 1 of an implant according to the invention with extremely small length (height)

The implant in FIG. 2 has very small length (height) in relation to the width thereof. The implant is quite recently screwed into the jaw bone and one observes the space immediately below the ceiling of the implant which has not yet been filled with bone but contains blood and other healing components from the produced surgical wound in the bone. However, after healing for some time the space will be completely filled with bone, FIG. 3.

Figure 3:
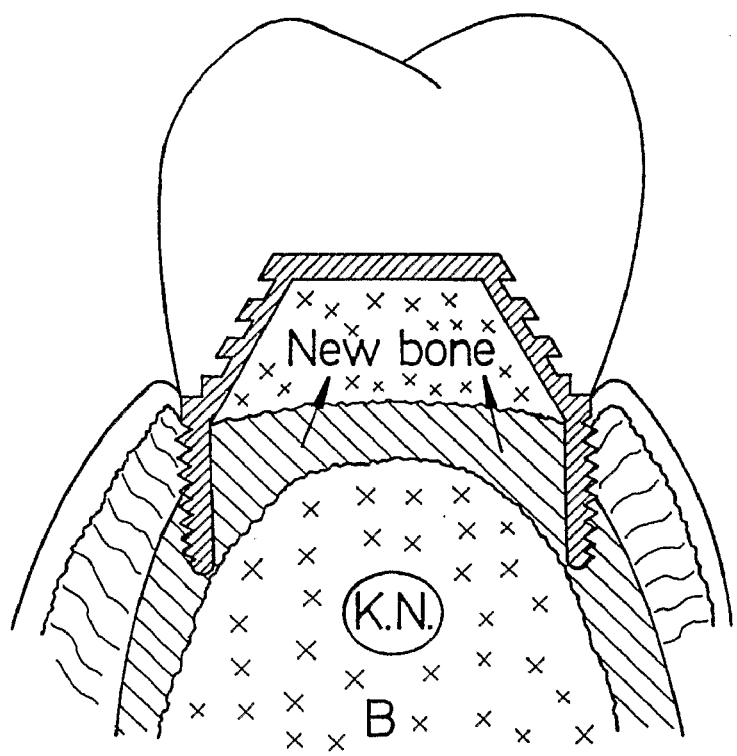
FIG. 3 is a view similar to FIG. 2 after integration for some time.

In FIG. 3 there is shown a tubular implant having the same length as that in FIG. 2 but with larger diameter. The bone B after some weeks to months has grown into the uppermost portion of the lumen of the implant closed at the top in contact with the cone or cupola shaped ceiling and as a consequence thereof the bone contact of the implant has increased further. A tooth crown TK has been cemented to the implant. Observe that the implants according to both FIG. 2 and FIG. 3 are substantially anchored in the outer compact bone.

Figure 4:
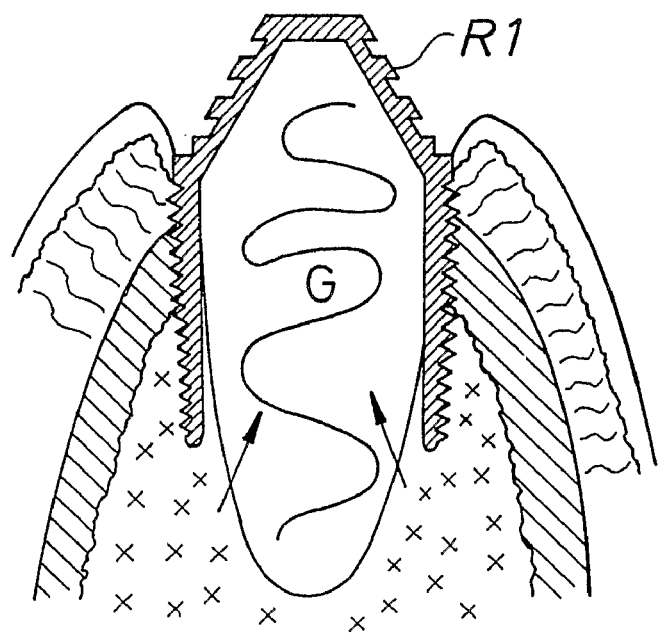
FIG. 4 is a similar view as FIG. 1 and discloses an implant according to the invention installed in a bone cavity after just previously effected tooth extraction.
Figure 5:
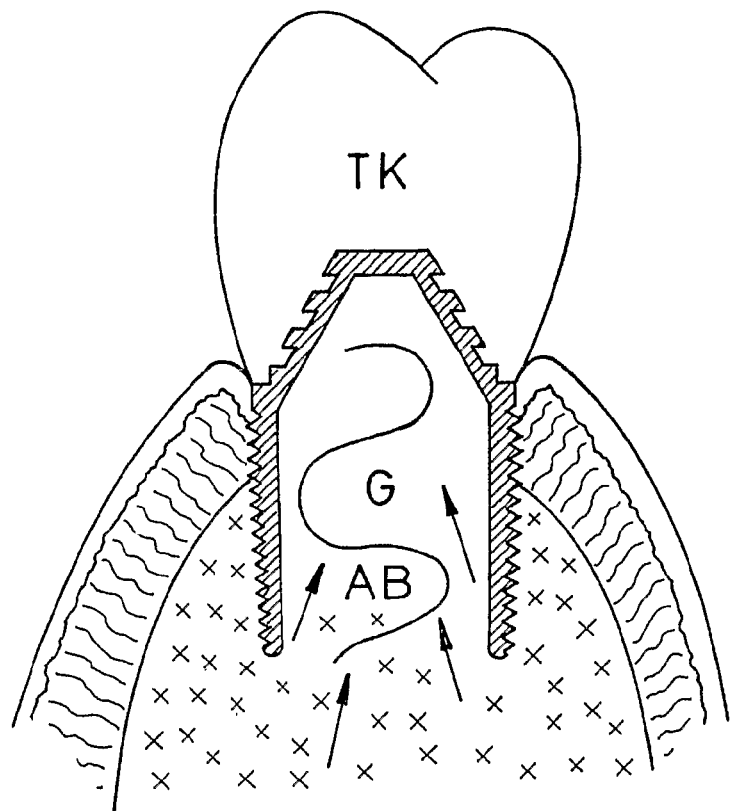
FIG. 5 is a view of the implant in FIG. 4 with mounted tooth crown.

The implant according to the invention can also advantageously be placed directly in a tooth alveolus immediately after tooth extraction or after alveol healing for one or two weeks, which is shown in FIG. 4 where the tubular implant R1 is installed in a bone crest with the alveolus filled with granulation tissue G after a quite recently effected tooth extraction. If the diameter of the implant is adjusted such that the outer diameter thereof is almost as large as or larger than the upper (marginal) diameter of the alveolus the side wall surface of the implant further down (apically) will be surrounded by bone at the inside as well as the outside and eventually will be filled in the lumen thereof by bone ingrowth from the alveolus walls and the alveolus bottom. This is shown in FIG. 5 where the alveolus is completely filled with bone AB as is the entire lumen of the implant including the uppermost portion ÖDB. The implant is provided with a tooth crown TK.

A special advantage of the possibility to place an implant in an alveolus immediately after or in an early stage after tooth extraction is that it is easy to orient oneself both sidewise and along the height. In the side portion of the upper jaw below the jaw cavities there is the additional advantage that the implant can be anchored in a bone structure which if it is not utilized often tends to be resorbed so that a considerable bone height is lost sometimes so clear that there is no more than one or two millimeters bone left below the jaw cavities.

Figure 6:
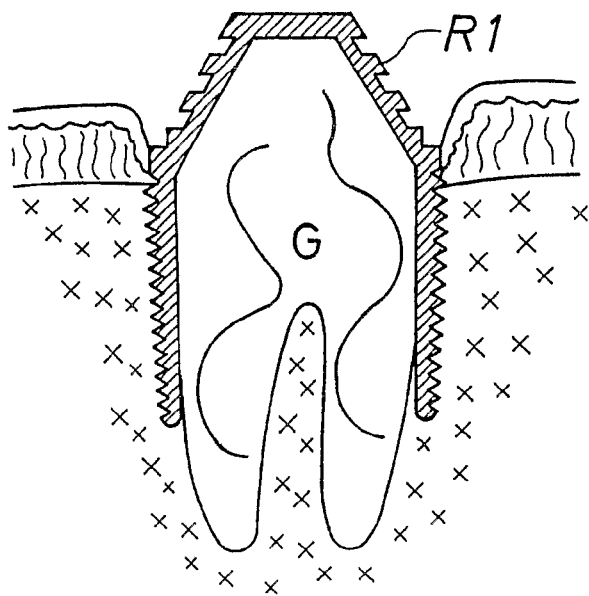
FIG. 6 is a similar view as FIG. 4 and discloses an implant which is inserted into an alveolus after extraction of a two-root tooth.
Figure 7:
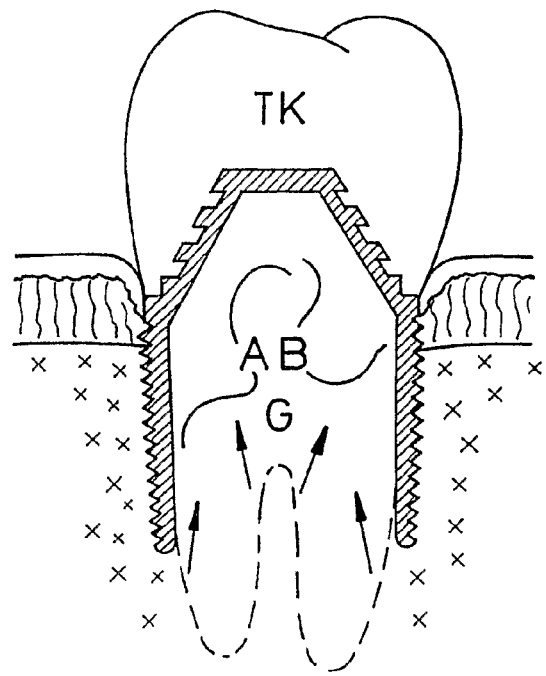
FIG. 7 is a view similar to FIG. 6 after the lumen of the implant has been completely filled with bone.

Teeth which have several roots such as some forward cheek teeth and the majority of the rear cheek teeth generally have such a bone anatomy that it is particularly favorable to a tubular implant of the type presented herein. In alveoli of teeth having several roots there is namely always in the apical (deepest) portion thereof a central bone portion formed as a ridge or a triangle of the bone located between the tooth roots. If compact implants were to be installed in such an alveolus it should either be necessary to place two implants (two-root teeth) or three implants (three-root teeth) or to place an implant having a very large diameter centrally in the alveolus and it would be necessary to remove the bone ridge or bone triangle by drilling. The tubular implant presented herein can be placed centrally in the alveolus while maintaining said bone ridge. This provides a primary stability, which is unique and moreover the bone ridge can relatively immediately deliver new bone cells and thus new bone for filling of the lumen of the implant. FIG. 6 discloses an alveolus after extraction of a two-root tooth in bone crest where the implant R1 according to the invention has been installed. According to FIG. 7 the alveolus and the total lumen of the implant are filled with bone, AB and ÖDB.

Figure 8:
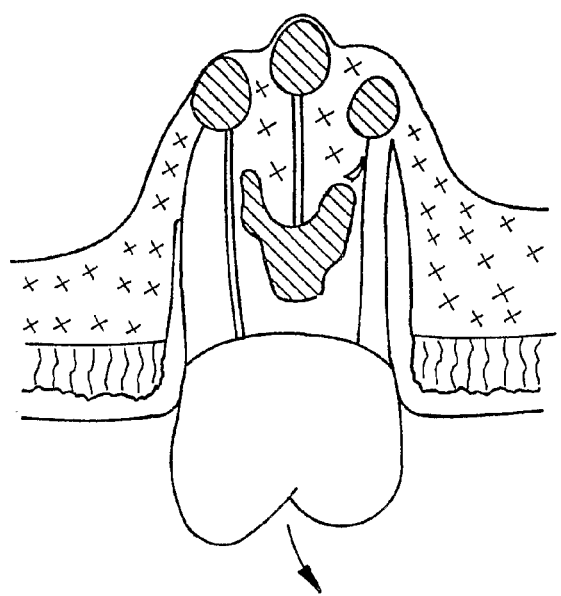
FIG. 8 is vertical cross-sectional view of a tooth in the upper jaw with infected roots and damages in the tooth attachment.
Figure 9:
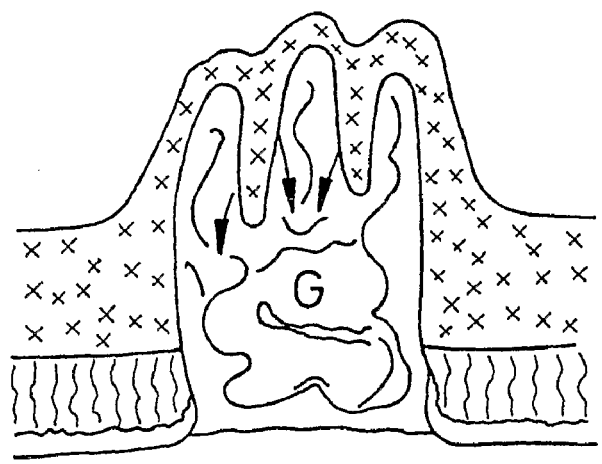
FIG. 9 is a vertical cross-sectional view of the alveolus in FIG. 8 after tooth extraction.
Figure 10:
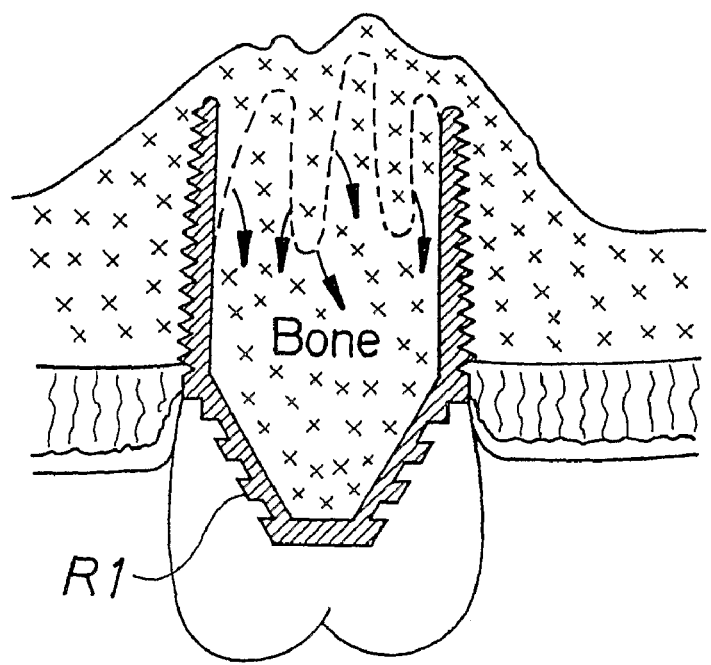
FIG. 10 is a view similar to FIG. 9 with an implant according to the invention inserted into the alveolus.
Figure 11:
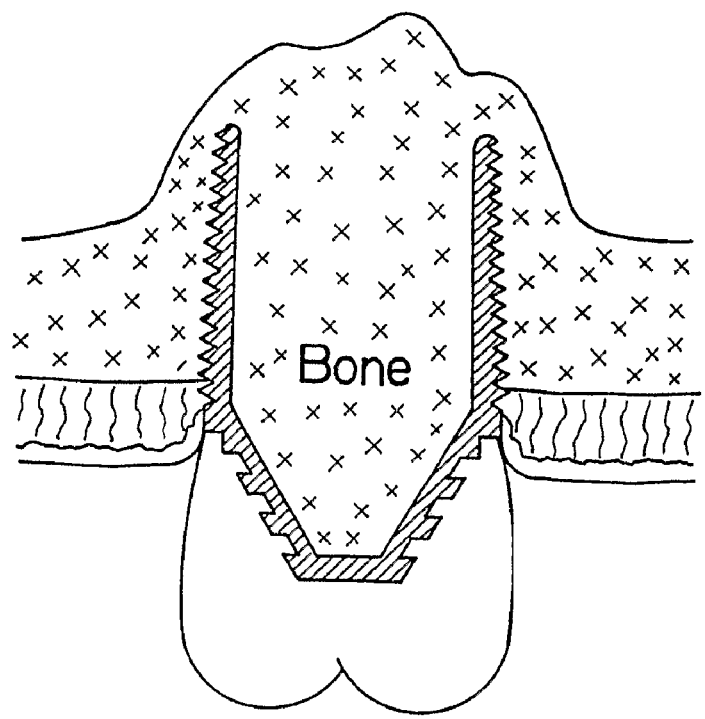
FIG. 11 is view similar to FIG. 10 after the lumen of the implant having been filled with bone.

FIG. 8 discloses a tooth of the upper jaw with infected roots and damages in the tooth attachment. The tooth is extracted and after extraction the alveolus is filled with granulation tissue G just about to heal, FIG. 9. As is shown in FIG. 10 a tubular implant R1 is inserted into the alveolus, which is under healing. Eventually the total alveolus and the lumen of the implant is filled with bone, FIG. 11.

Figure 12:
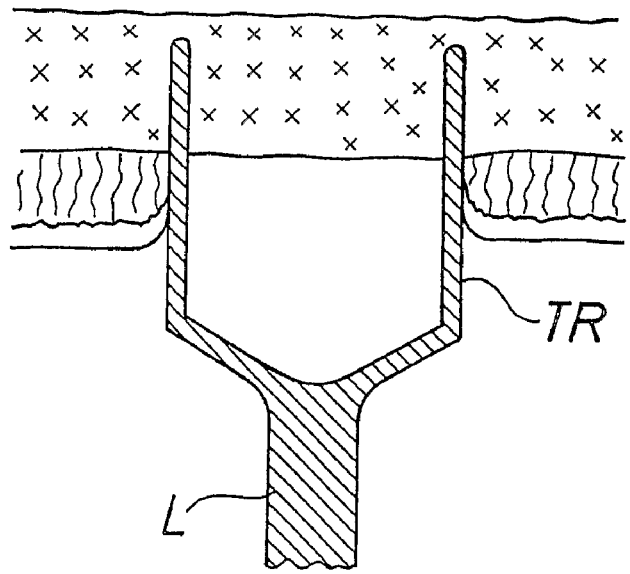
FIG. 12 is a vertical cross-sectional view, which discloses trephine drilling of bone in the upper jaw.
Figure 13:
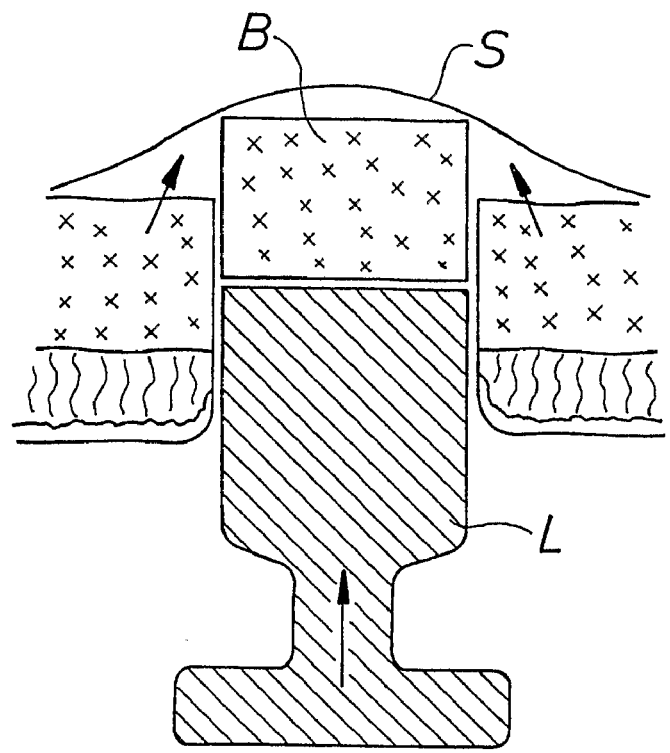
FIG. 13 is a vertical cross-sectional view, which illustrates that a bone pin and a sinus mucous membrane are being hacked up by means of a lifter after the trephine drilling in FIG. 12.
Figure 14:
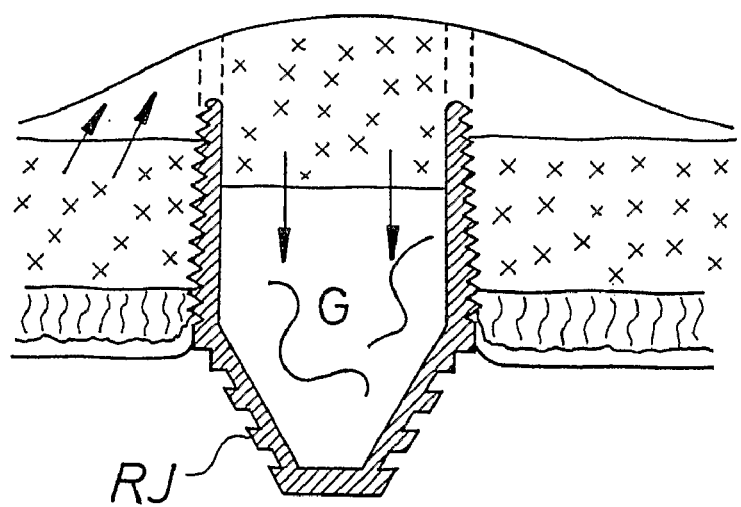
FIG. 14 is a view similar to FIG. 13 with an implant according to the invention screwed in at the location thereof.
Figure 15:
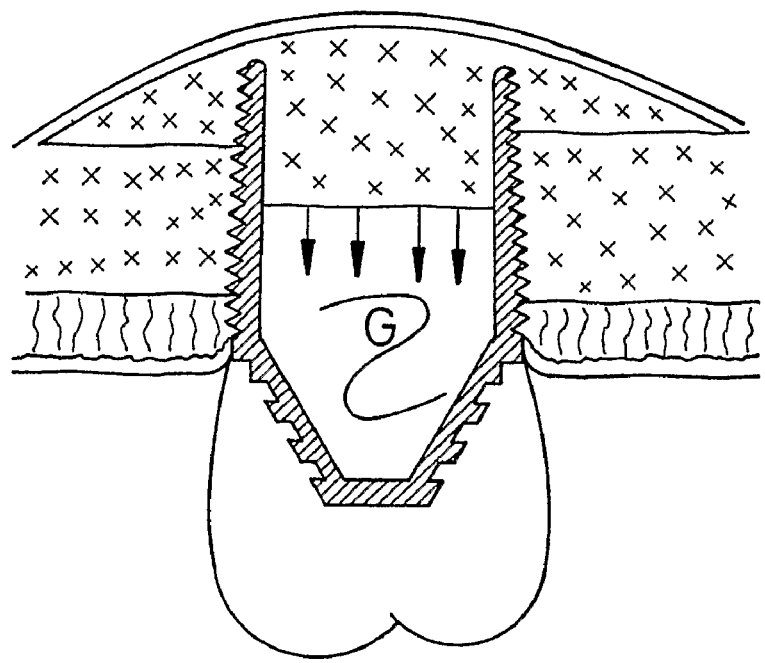
FIG. 15 is a view similar to FIG. 14 with the implant completely filled with bone.

If one faces a situation with very small bone height under the jaw cavities the tubular implant disclosed herein can be used for lifting the mucous membrane of the jaw cavity simultaneously as the implant is being installed. The procedure is that there is drilled according to FIG. 12 a trephine groove with a trephine drill TR to a position just under the mucous membrane of the jaw cavity. Then, a thin bone layer B is hacked or pressed to the bottom of the groove by means of a lifter L together with the sinus mucous membrane S and the bone cylinder which is attached to the mucous membrane and has been removed from other bone by drilling into the jaw cavity, FIG. 13. Then the implant RJ is installed, FIG. 14, the implant maintaining the mucous membrane with the bone pin in the intended position. If the bone under the jaw cavity as an average is for example 3 mm thick (high) it is easy to install a tubular implant which is 6 mm in length and thus lifts the mucous membrane and the bone pin 3 mm. The space which is then created below the lifted mucous membrane beside the bone pin will be filled with the coagulated blood which transforms into healing tissue (FIG. 15) which rather rapidly will be converted into bone. It is also possible to place corporal bone and bone substitute both in the tubular implant before it is installed and in the bone cavity created below the mucous membrane of the jaw cavity around the implant but bone formation will take place also without these measures. This has been shown i.e. by Lundgren S. et al (2003) with a compact cylindrical implant. They lifted the mucous membrane of the jaw cavity by means of surgical operation with so called window technique where a window is drilled to the jaw cavity via the outer sidewall thereof. The advantages with the implant presented herein is that it is not necessary to open a bone window, that a smaller amount bone has to be removed by drilling and that a tubular implant having a larger diameter than conventional cylindrical implants, with the side wall surface thereof will be closer to the buccal and lingual side walls of the jaw cavity, which increases the primary stability, and that the implant as such is used for lifting the mucous membrane.

Figure 16:
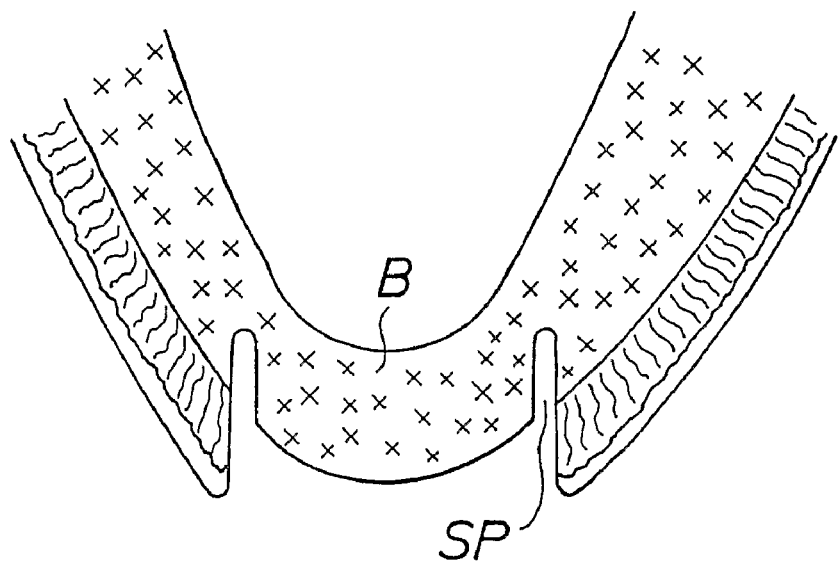
FIG. 16 is a transverse cross-sectional view of an upper jaw with jaw cavity after trephine drilling in the jaw bone.
Figure 17:
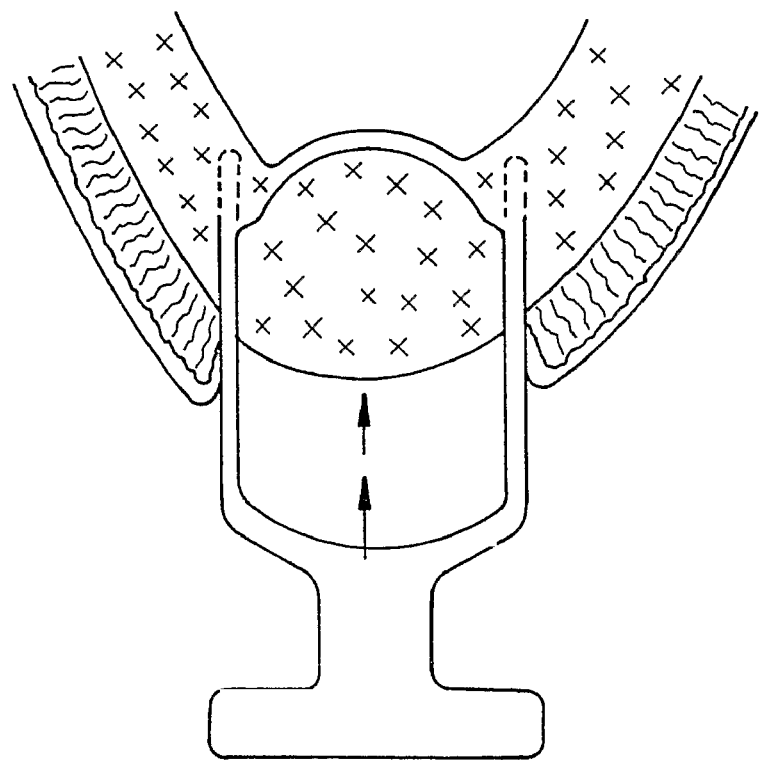
FIG. 17 is a transverse cross-sectional view similar to FIG. 16 during lifting of the jaw cavity mucous membrane by means of a curved lifter.
Figure 18:
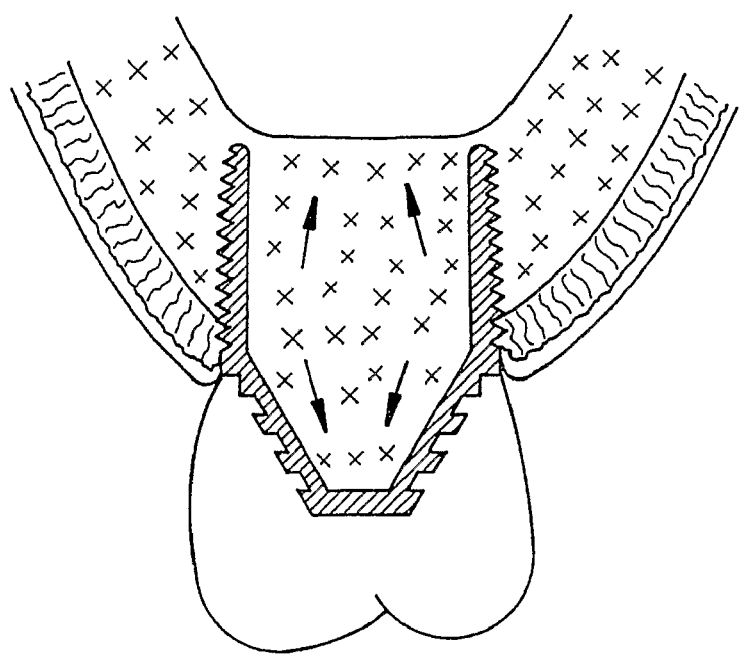
FIG. 18 is a transverse cross-sectional view similar to FIG. 17 after insertion of an implant according to the invention the implant being filled with bone.
Figure 19:
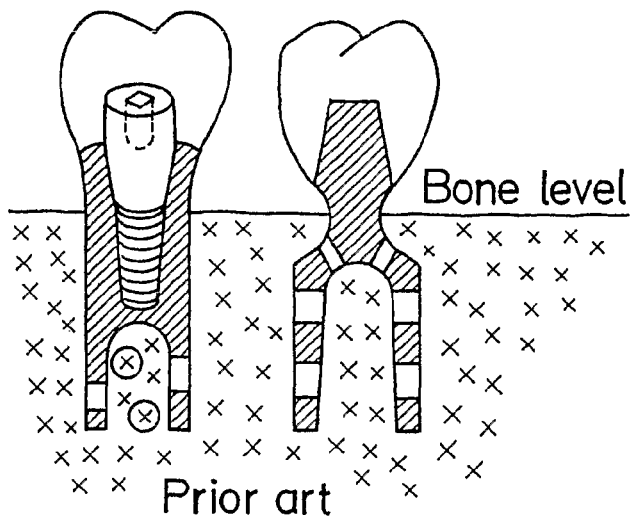
FIG. 19 is a vertical cross-sectional view of an implant according to the state of the art with an attached tooth crown.
Figure 20:
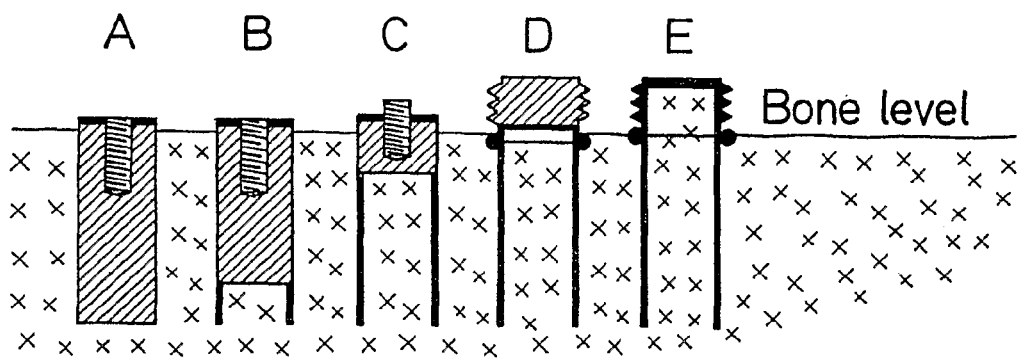
FIG. 20 is an explanatory sketch for contact between bone and implant for different implant types.

FIG. 16 to 18 discloses a special technique for insertion of the implant according to the invention in the bone of the upper jaw below the jaw cavity and the integration into this jaw bone. The soft tissue which covers the jaw bone (B) has been punched away so that the bone where the implant is to be located (the implant seat) has been uncovered (FIG. 16). In the illustrated example the bone has a relatively smooth surface perpendicularly to the direction for inserting the implant but is not thicker than about 3 mm. After the centre of the implant seat has been marked by means of a small round drill the groove Sp into which the implant is to be screwed is drilled by means of a trephine drill to the desired depth. By means of a lifter having ears the mucous membrane of the jaw cavity is lifted, FIG. 17, and then the trephine groove can be made deeper, so that a tubular implant with a thread height of 6 mm, FIG. 18, can be screwed in to the intended position by means of an implant carrier/tightener which has an inner hex which matches the outer hex surfaces 6 of the tower. The implant is installed with a torsional force, which usually amounts to 30 to 40 Ncm. If the implant is not self-tapping a screw tap is needed which either can be double, i.e. can cut in both the outer and the inner wall of the trephine groove, or can cut only in the outer wall. According to illustration by means of arrows in FIG. 18 bone will grow into the base portion of the implant as well as the tower thereof. FIGS. 19 and 20*a, b, c* shows prior art, while FIG. 20*d, e* discloses the situation after some months when bone tissue fills the total implant over the original bone level of the implant seat.

It should be noted that the trephine drill in some situations can be so dimensioned in relation to the inner sidewall of the implant and the thread tap that there will be a clearance of about 0.1 mm (0.05+0.05 mm) between these and the inner bone wall of the groove. This is made in order not to risk that the bone pin (B) will be broken and come loose at drilling if the spongy bone is considered to have very low density or the pin is very narrow. Previous studies have shown that such a small distance does not prevent a normal oseo integration, i.e. intimate healing of the bone tissue directly against the implant wall.

The invention claimed is:

1. A dental implant for supporting a dental restoration in a jawbone, the dental implant comprising:
    a body extending along a longitudinal axis and having a coronal end and an apical end, the coronal end forming, in part, a coronal surface that extends generally transverse to the longitudinal axis and the apical end, in part, forming an annular surface that extends generally transverse to the longitudinal axis;
    an external surface extending between the coronal surface and the annular surface and generally facing away from the longitudinal axis of the dental implant, the external surface including a threaded surface that extends substantially to the apical end of the body;
    a first inner surface concentric with the external surface, the first inner surface generally facing toward the longitudinal axis of the dental implant, at least a portion of the first inner surface including internal grooves in the first inner surface that do not extend completely through the body to the external surface, the first inner surface defining an opening facing in an apical direction; and
    a second inner surface that intersects with the first inner surface along an outer circumference of the second inner surface and extends generally transverse to the longitudinal axis of the dental implant and faces in a generally apical direction;
    wherein the dental implant is sized and configured to be implanted in a patient's jawbone.

2. The dental implant according to claim 1, further comprising a stop mark disposed along the external surface for defining an end position for the dental implant at insertion into the jawbone wherein the stop mark is formed by a shoulder which can be engaged with the bone tissue.

3. The dental implant according to claim 2 wherein the shoulder is formed by the end wall portion.

4. The dental implant according to claim 3, wherein the shoulder is formed toward the coronal end.

5. The dental implant according to claim 1 wherein the threaded surface includes double threading.

6. The dental implant according to claim 1, wherein the internal grooves on the first inner surface form a threaded surface.

7. The dental implant according to claim 1, wherein the internal grooves are micro threads.

8. The dental implant according to claim 1, in combination with a trephine drill.

9. The dental implant according to claim 1, wherein the internal grooves extend in a vertical direction parallel to the longitudinal axis.

10. The dental implant according to claim 1, in combination with a dental component.

11. The dental implant according to claim 10, wherein the dental component is a tooth prosthesis.

12. The dental implant according to claim 10, wherein the dental component is a crown.

13. The dental implant according to claim 10, wherein the dental component is a prosthetic component.

14. The dental implant of claim 1, wherein the implant has a length of between about 2 to about 16 millimeters.

15. The dental implant of claim 1, wherein the implant has a length of between about 3 to about 8 millimeters.

16. The dental implant of claim 1, wherein the first inner surface has a cone shape.

17. The dental implant of claim 1, wherein the first inner surface has a cylindrical shape.

18. The dental implant of claim 1, wherein the external surface includes a side surface between the threaded surface and the coronal end.

19. The dental implant of claim 18, wherein the side surface includes grooves or ridges.

20. A method of installing a dental implant comprising:
    inserting the implant into a patient's jawbone, the implant comprising:
        a body extending along a longitudinal axis and having a coronal end and an apical end, the coronal end forming, in part, a coronal surface that extends generally transverse to the longitudinal axis and the apical end, in part, forming an annular surface that extends generally transverse to the longitudinal axis;
        an external surface extending between the coronal surface and the annular surface and generally facing away from the longitudinal axis of the dental implant, the external surface including threads that extend along the external surface about a longitudinal axis of the implant;
        a first inner surface concentric with the external surface, the first inner surface generally facing toward the longitudinal axis of the dental implant, at least a portion of the first inner surface including grooves that form a grooved surface, the grooves not extending through the body of the implant to the external surface, and the first inner surface defining an opening facing in an apical direction; and
        a second inner surface that intersects with the first inner surface along an outer circumference of the second inner surface and extends generally transverse to the longitudinal axis of the dental implant and faces in a generally apical direction.

21. The method according to claim 20, wherein the implant further comprises a stop mark disposed along the external surface for defining an end position for the dental implant at insertion into the jawbone wherein the stop mark is formed by a shoulder which can be engaged with the bone tissue.

22. The method according to claim 21 wherein the shoulder is formed by the end wall portion.

23. The method according to claim 22, wherein the shoulder is formed toward the coronal end.

24. The method according to claim 20 wherein the threads on the external surface includes double threading.

25. The method according to claim 20, wherein grooves on the first inner surface form a threaded surface.

26. The method according to claim 20, wherein the grooves are micro threads.

27. The method according to claim 20, wherein installing the dental implant is in combination with a trephine drill.

28. The method according to claim 20, wherein the grooves extend in a vertical direction parallel to the longitudinal axis.

29. The dental implant of claim 1, wherein the grooves are horizontal.

30. The method according to claim 20, wherein installing the dental implant is in combination with a dental component.

31. The method according to claim 30, wherein the dental component is a crown.

32. The method according to claim 30, wherein the dental component is a tooth prosthesis.

33. The method according to claim 30, wherein the dental component is a prosthetic component.

34. The method of claim 20, wherein the implant has a length of between about 2 to about 16 millimeters.

35. The method of claim 20, wherein the implant has a length of between about 3 to about 8 millimeters.

36. The method of claim 20, wherein the first inner surface has a cone shape.

37. The method of claim 20, wherein the first inner surface has a cylindrical shape.

38. The method of claim 20, wherein the external surface includes a side surface between the threaded surface and the coronal end.

39. The method of claim 38, wherein the side surface includes grooves or ridges.

40. The method of claim 20, wherein the grooves are horizontal.

41. The method of claim 20, wherein the threads on the external surface extend to the apical end of the dental implant and the grooved surface extends longitudinally from the apical end toward the coronal end of the dental implant, wherein at least a portion of the threads on the external surface overlap at least a portion of the grooves on the first inner surface in the longitudinal direction.

42. A dental implant for supporting a dental restoration in a jawbone, the dental implant comprising:
   a body extending along a longitudinal axis and having a coronal end and an apical end, the coronal end forming, in part, a coronal surface that extends generally transverse to the longitudinal axis and the apical end, in part, forming an annular surface that extends generally transverse to the longitudinal axis;
   an external surface extending between the coronal surface and the annular surface and generally facing away from the longitudinal axis of the dental implant, the external surface including threads that extend along the external surface around a longitudinal axis of the implant;
   a first inner surface concentric with the external surface, the first inner surface generally facing toward the longitudinal axis of the dental implant, at least a portion of the first inner surface including grooves that form a grooved surface, the grooves not extending through the body of the implant to the external surface, the first inner surface defining an opening facing in a generally apical direction;
   a second inner surface that intersects with the first inner surface along an outer circumference of the second inner surface and extends generally transverse to the longitudinal axis of the dental implant and faces in the generally apical direction; and
   a dental component coupled to the coronal end of the implant.

43. The dental implant according to claim 42, further comprising a stop mark disposed along the external surface for defining an end position for the dental implant at insertion into the jawbone wherein the stop mark is formed by a shoulder which can be engaged with the bone tissue.

44. The dental implant according to claim 43, wherein the shoulder is formed by the end wall portion.

45. The dental implant according to claim 44, wherein the shoulder is formed toward the coronal end.

46. The dental implant according to claim 42, wherein the threads on the external surface includes double threading.

47. The dental implant according to claim 42, wherein the length of the implant is substantially equal to the diameter.

48. The dental implant according to claim 42, wherein the implant has a diameter, which is larger than its length.

49. The dental implant according to claim 42, wherein grooves on the first inner surface form a threaded surface.

50. The dental implant according to claim 49, wherein the threads on the first inner surface are micro threads.

51. The dental implant according to claim 42, wherein the grooves are micro threads.

52. The dental implant according to claim 42, in combination with a trephine drill.

53. The dental implant according to claim 42, wherein the grooves extend in a vertical direction parallel to the longitudinal axis.

54. The dental implant according to claim 42, wherein the dental component is a tooth crown.

55. The dental implant according to claim 42, wherein the dental component is a tooth prosthesis.

56. The dental implant of claim 42, wherein the implant has a length of between about 2 to about 16 millimeters.

57. The dental implant of claim 42, wherein the implant has a length of between about 3 to about 8 millimeters.

58. The dental implant of claim 42, wherein the first inner surface has a cone shape.

59. The dental implant of claim 42, wherein the first inner surface has a cylindrical shape.

60. The dental implant of claim 42, wherein the external surface includes a side surface between the threaded surface and the coronal end.

61. The dental implant of claim 60, wherein the side surface includes grooves or ridges.

62. The dental implant of claim 42, wherein the grooves are horizontal.

63. The dental implant of claim 42, further comprising:
   a third inner surface concentric with the external surface, the third inner surface generally facing toward the longitudinal axis of the dental implant, at least a portion of the third inner surface including threads; and
   a fourth inner surface that intersects with the third inner surface along an outer circumference of the fourth inner surface and extends generally transverse to the longitudinal axis of the dental implant and faces in a generally coronal direction.

64. The dental implant of claim 42, wherein the dental component is a restoration.

65. The dental implant of claim 42, wherein the dental component is an abutment.

66. A dental implant for supporting a dental restoration in a jawbone, the dental implant comprising:
   a body extending along a longitudinal axis and having a coronal end and an apical end, the coronal end forming, in part, a coronal surface that extends generally transverse to the longitudinal axis and the apical end, in part, forming an annular surface that extends generally transverse to the longitudinal axis;
   an external surface extending between the coronal surface and the annular surface and generally facing away from the longitudinal axis of the dental implant, the external surface including a threaded surface that extends substantially to the apical end of the body;
   a first inner surface concentric with the external surface, the first inner surface generally facing toward the longitudinal axis of the dental implant, at least a portion of the first inner surface including internal grooves in the first inner surface that do not extend completely through the body to the external surface, the first inner surface defining an opening facing in an apical direction; and
   a second inner surface that intersects with the first inner surface along an outer circumference of the second inner surface and extends generally transverse to the longitudinal axis of the dental implant and faces in a generally apical direction;
   wherein the external surface of the body has a micro topography which promotes bone formation.

* * * * *